United States Patent
Al-Rashdan

(10) Patent No.: US 7,824,357 B2
(45) Date of Patent: Nov. 2, 2010

(54) METHOD AND SYSTEM FOR PREVENTING CONTRAST ASSOCIATED NEPHROPATHY

(76) Inventor: Ibrahim Rashid Al-Rashdan, P.O. Box 24923, Safat 13110 (KW)

(*) Notice: Subject to any disclaimer, the term of this patent is extended or adjusted under 35 U.S.C. 154(b) by 520 days.

(21) Appl. No.: 11/761,049

(22) Filed: Jun. 11, 2007

(65) Prior Publication Data
US 2008/0306425 A1   Dec. 11, 2008

(51) Int. Cl.
*A61M 37/00* (2006.01)
*A61M 29/00* (2006.01)

(52) U.S. Cl. .............. 604/6.09; 604/4.01; 604/6.16; 604/101.01; 604/103.07

(58) Field of Classification Search ............ 604/4.01, 604/5.01, 5.04, 6.09, 6.11, 96.01, 101.01, 604/103.07, 6.16
See application file for complete search history.

(56) References Cited

U.S. PATENT DOCUMENTS

| | | | | | |
|---|---|---|---|---|---|
| 4,820,261 | A | * | 4/1989 | Schmoll et al. | 604/5.01 |
| 5,411,479 | A | * | 5/1995 | Bodden | 604/101.03 |
| 6,554,819 | B2 | * | 4/2003 | Reich | 604/508 |
| 6,585,689 | B1 | * | 7/2003 | Macoviak et al. | 604/103.07 |
| 7,163,520 | B2 | * | 1/2007 | Bernard et al. | 604/6.09 |

* cited by examiner

*Primary Examiner*—Leslie R Deak
(74) *Attorney, Agent, or Firm*—Lowe Hauptman Ham & Berner, LLP

(57) ABSTRACT

A method for preventing contrast associated nephropathy includes the steps of providing a multi-lumen dual balloon catheter and inserting the catheter into a patient's coronary sinus. The method also includes the steps of inflating the two balloons to block blood flow from the coronary sinus into the right atrium and draining blood containing contrast solution from between the two balloons through the catheter while the blood flow is blocked. A hemo filtration unit is used to remove contrast solution from the drained blood and the filtered blood returned to the right atrium. A multi-lumen dual balloon catheter is also disclosed.

5 Claims, 7 Drawing Sheets

METHOD AND SYSTEM FOR PREVENTING CONTRAST ASSOCIATED NEPHROPATHY

FIELD OF THE INVENTION

This invention relates to a method and system for preventing contrast associated nephropathy and more particularly to a method and system utilizing a dual-balloon device to ensure contrast drainage from the upper sinus veins while a larger tapered ostium balloon acts to drain the contrast from the interior vein by creating a negative pressure in a semi-closed chamber between two balloons.

BACKGROUND FOR THE INVENTION

Percutaneous transluminal coronary angioplasty is frequently used in treating coronary atherosclerosis which produces areas of blockage within a coronary artery. However, before performing percutaneous transluminal coronary angioplasty, and during the procedure itself, iodine containing dye or other contrast material is injected into a patient's artery through a catheter. This iodine solution is fluorescent and enables the coronary arteries to be clearly illustrated for the physician.

However, there is one serious problem associated with the use of contrast solutions. The problem is that the use of such solutions may lead to contrast induced nephropathy. Contrast induced nephropathy can result in transient or permanent renal impairment or failure of a patient's kidneys. It is well known that renal dysfunction is associated with the use of radio graphic contrast media and that the dysfunction may range from a transient slight increase in serum creatinine levels to renal failure requiring transient or long-term dialysis.

Many patients require revascularization of more than a single vessel. However, when there is danger of contrast induced renal failure, the vessels are done on separate procedures at greatly increased cost and additional risk of arterial puncture. Therefore, it is highly desirable or imperative to eliminate the risk of renal failure.

Further, there are many other patients with chronic renal insufficiencies who must wait 24 to 48 hours in the hospital before undergoing percutaneous transluminal coronary angioplasty in order to space the kidney load associated with the contrast load. Still others, particularly the elderly with a pre-existing renal insufficiency make up a large group in which angioplasty is avoided because multi-vessel disease and multi-vessel intervention may lead to renal failure.

In view of the above, several attempts have been made to prevent contrast associated nephropathy. For example, a U.S. Pat. No. 6,554,819 discloses a method and device for preventing contrast associated nephropathy. As disclosed therein, when a contrast solution is injected into the coronary artery of a patient, blood is prevented from flowing through the coronary sinus into the right atrium. The blood in the coronary sinus is bypassed to a filtration device which filters out the contrast solution from the blood and re-circulates the blood back to the patient. Preferably, blood flow from the coronary sinus is blocked by a balloon catheter which includes a port distal of the balloon so that when the sinus is occluded, blood flows from the sinus into the central lumen of the catheter where it can be directed to the filtration device.

A more recent approach for removal of radio-contrast media from blood is set forth in a U.S. Pat. No. 7,163,520 of Bernard et al. The Bernard patent discloses an extra corpeal blood circuit for removal of contrast from human blood using a filter and withdraw filter pump and a bypass pump. The withdrawal filter blood pump operates when a contrast bolus has been detected. Otherwise, the bypass blood pump maintains physiological blood flow from the coronary sinus preventing the need for deflation and re-inflation of the balloon catheter. When contrast is detected in the patient's blood, the bypass blood pump is stopped to prevent contrast from leaking back into the patient's circulatory system via the bypass pump and coronary sinus blood flow is maintained at its physiological blood flow resulting in the heart being oblivious to the transition by the pre-filter blood pump.

Notwithstanding the above, it is presently believed that there is a need for an improved method and system for preventing contrast associated nephropathy. There should be a need since the method and apparatus in accordance with the present invention facilitates removal of the contrast media and at the same time reduces the risk of contrast associated nephropathy. Therefore, it is believed that more procedures can be completed on patients that are at risk for renal damage.

BRIEF SUMMARY OF THE INVENTION

The dye drain system in accordance with the present invention provides near total removal of contract solution from the systematic circulation prior to its arrival to the kidneys and hence provides protection due to the absence of dye exposure. This is dependent on the utilization of the coronary sinus system which drains into the right atrium. The system is designed to seal the drainage in the coronary sinus with a double balloon system which ensures drainage of the anterior and inferior veins. The challenge of the current occlusion devices of the coronary sinus is the contrast escape from the inferior vein which is the largest of all coronary veins and close to the coronary ostium preventing any occlusion device placement. Therefore, the double balloon system with differential size will ensure contrast drainage from the upper veins while a larger tapered ostium balloon is anchored near the ostium by the smaller balloon and acts to drain the contrast from the inferior vein by creating negative pressure in the semi-closed chamber in between the two balloons.

Therefore, the system will work for coronary interventions, with transient occlusion of the coronary sinus after each contrast injection and subsequent drainage of the contrast containing blood from its central lumen for disposal and hence protecting kidneys from the deleterious effects of the angiographic contrast material. For continuous occlusion of the coronary sinus ostium, in some cases where more attention is needed to the interventional procedure rather than the drainage system a modification with a hemofiltration active continuous suction system is used.

In essence the present invention contemplates a method for preventing contrast associated nephropathy using a multi-lumen dual balloon catheter. The dual balloon catheter is inserted into or adjacent a patient's coronary sinus and the blood flow from the coronary sinus into the right atrium of the heart is blocked. Blood containing a contrast solution between the two balloons is then drained through the catheter while the blood flow to the right atrium is blocked.

In a first embodiment of the invention the method includes providing a multi-lumen dual balloon catheter having a first lumen, a larger tapered balloon and a smaller spherical balloon connected to the larger tapered balloon by the first lumen. In this embodiment, an orifice is defined in the first lumen between the two balloons. In this embodiment, the catheter also includes a first inflation port for the larger tapered balloon and a second inflation port for the smaller spherical balloon and a third lumen connected to the port for removing blood containing a contrast solution from between the two balloons. In this method, the balloons are inflated after introducing a contrast solution into a patient's bloodstream and blood containing contrast solution is removed from between the two balloons.

Further in a preferred form of the first embodiment of the invention a hemo-filtration unit is provided and the blood removed from between the two balloons is filtered to remove the contrast solution and the filtered blood returned to the patient's right atrium.

A further embodiment of the invention contemplates a method that includes the steps of providing a hemo-filtration unit, a triple lumen dual balloon catheter having a first balloon adapted to occlude a portion of a patient's coronary sinus at the Atrioventricular Groove. A first inflation port is provided and a first balloon connected to the first inflation port for inflating the first balloon to occlude a first portion of the patient's sinus.

The Atrioventricular groove is between the atria and the ventricular of the heart where the main trunk of the coronary sinus lies with its branches extending to the heart.

Also provided are a second balloon adapted to occlude a second portion of the patient's sinus including the inferior cardiac vein. In this embodiment of the invention, the method includes the step of providing a pair of drainage ports with one of the drainage ports disposed in a first portion of the patient's sinus adjacent to the first balloon and the second drainage port disposed in the inferior cardiac vein adjacent to the second balloon. A suction port and a third lumen connects the suction port to the first and second drainage ports for removing blood containing contrast solutions from the patient's coronary sinus ostium. A second smaller generally spherical balloon is provided for positioning within the patient's coronary sinus and for anchoring the first larger tapered balloon in place. A lumen including a tip that extends through both balloons and a first port between the first and second balloons are also provided. The catheter also includes first means for inflating and deflating the first tapered balloon and a second means for inflating and deflating the second balloon and means for creating a negative pressure between the balloons for draining blood containing contrast media thorough the suction port.

The invention will now be described in connection with the accompanying drawings wherein like numbers have been used to designate like parts.

DESCRIPTION OF THE PREFERRED EMBODIMENTS OF THE INVENTION

Contrast nephropathy can be prevented if the contrast solution is kept away from the kidney. However, once the dye has been mixed with blood the only way to separate the two is by filtration as for example dialyses. Dialyses relies on diffusion down a concentration gradient and is not completely effective if the concentration of dye in the blood to be filtered is low. Furthermore, the flow rates of conventional hemodialyses procedures are too high for patients who are undergoing angioplasty and these patients typically do not tolerate wide fluctuations in blood pressure as is common with hemodialyses.

Figure 1:
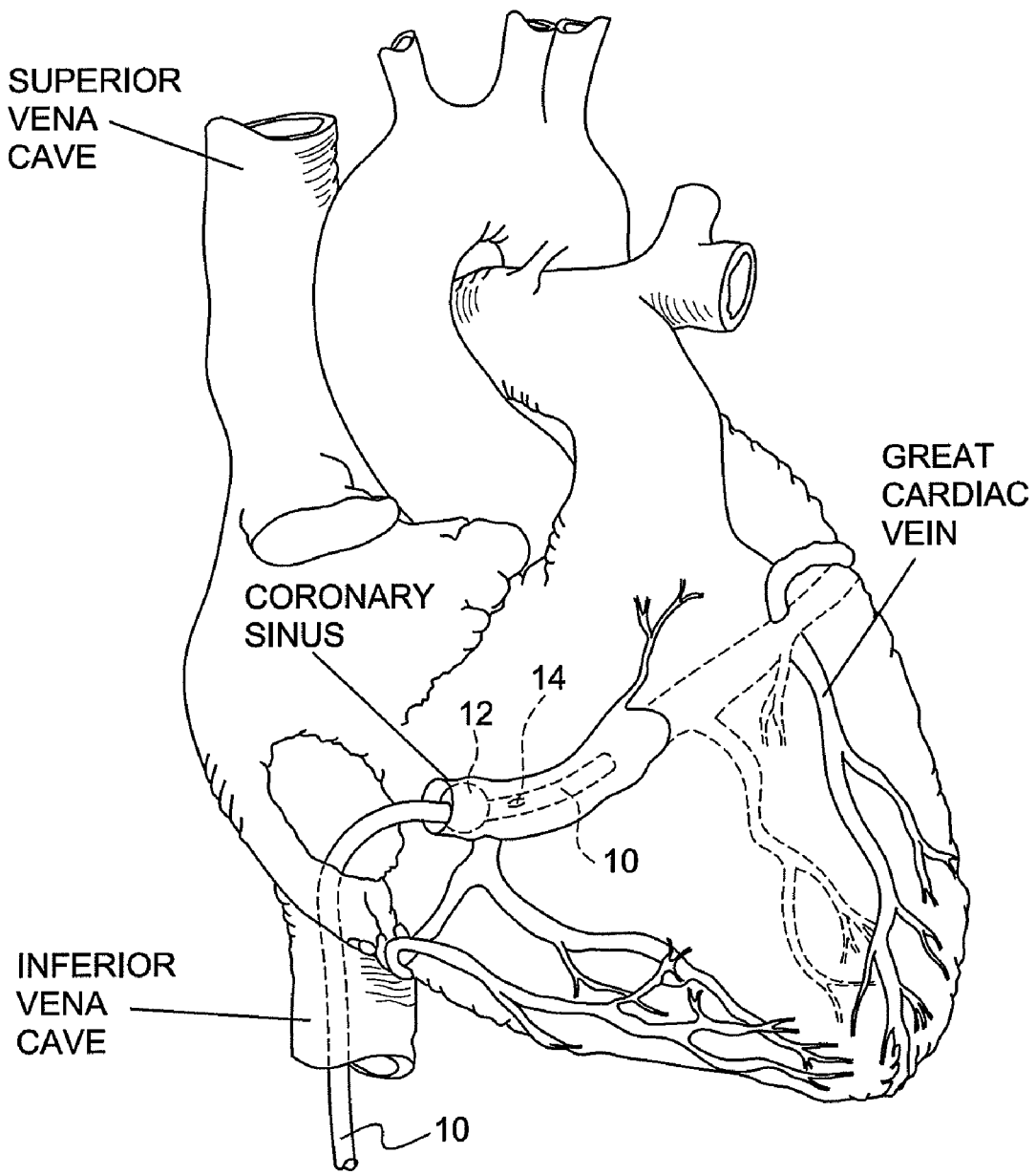
FIG. 1 is an anatomical view of a human heart depicting the coronary sinus and it's venus branches which empty into the right atrium and showing schematically the position of a prior art catheter.

In the prior art, the filtration of contrast solution from blood is done by placing a catheter in the coronary sinus where the concentration of dye is the highest. The catheter is provided with means for blocking the flow of blood to the right atrium while at the same time permitting the blood in the coronary sinus to be delivered through the catheter to a filtration machine as described in the aforementioned U.S. Pat. No. 6,554,819 which is incorporated herein in its entirety by reference. The way in which the prior art device is accomplished is explained with reference to FIG. 1. FIG. 1 illustrates a heart in which a catheter 10 has been introduced from the groin through the inferior vena cavity into the coronary sinus. The distal portion of the catheter 10 carries a balloon 12 which can be inflated and deflated as required. Balloon catheters as used therein are conventional. In addition to the balloon catheter 12, catheter 10 also includes a port 14 distal but close to the balloon which permits blood in the coronary sinus to drain into a catheter lumen when the balloon 12 occludes the coronary sinus.

Figure 2:
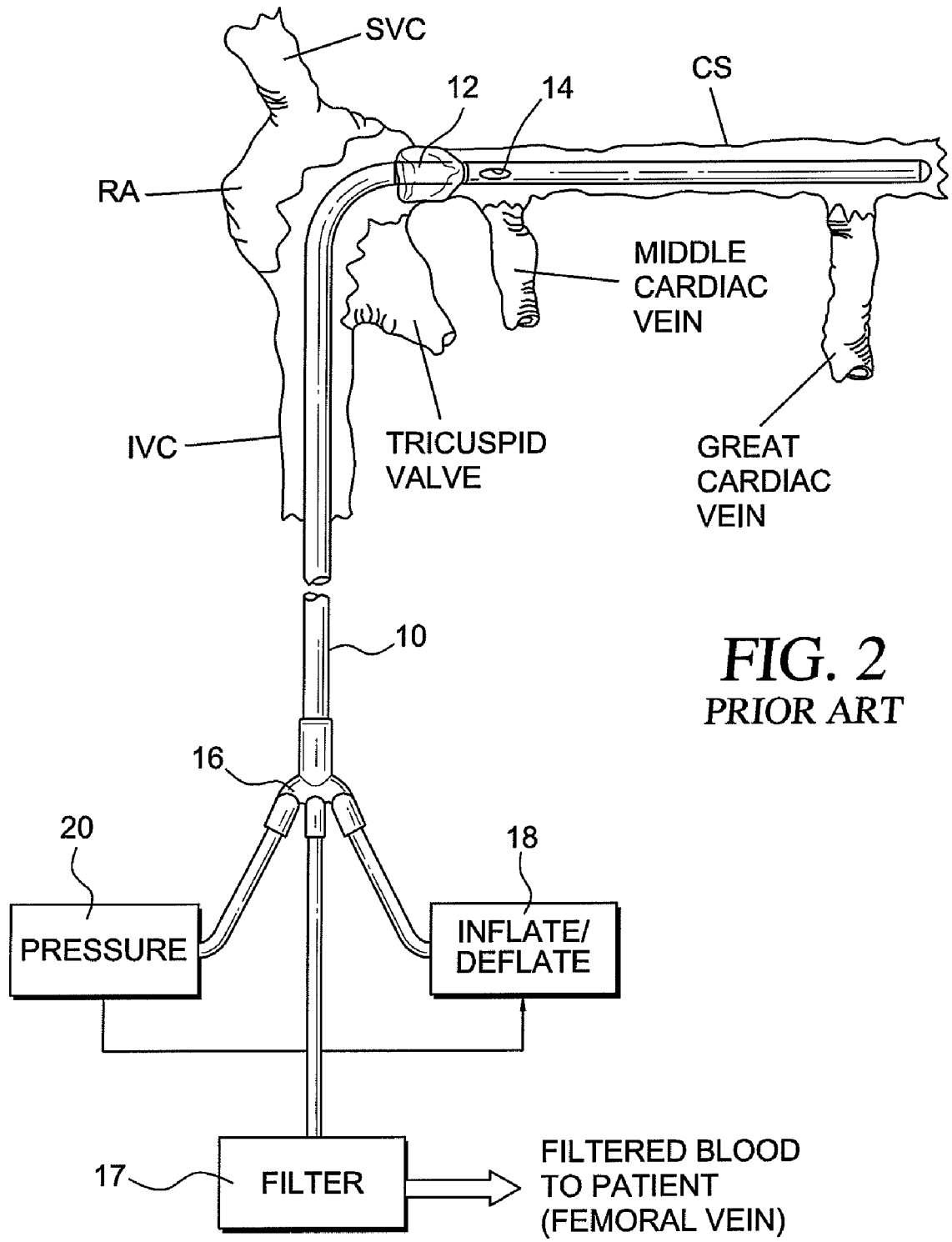
FIG. 2 is a schematic illustration of a prior art catheter and filtration unit for removing contrast solution from the blood that passes through a catheter.

FIG. 2 schematically shows the coronary sinus and right atrium of a heart. The catheter 10 is positioned preferably with its tapered distal end distal to the coronary sinus and balloon 12 expanded to block blood flow from the coronary sinus to the right atrium. As shown schematically, the proximal end of catheter 10 terminates in a y connector 16 which enables the central lumen of catheter 10 to be connected to a filtration device 17. Catheter 10 will also include an inflation lumen (not shown) which is connected by the connector 16 to a device 18 which can inflate and deflate balloon 12. Also, a pressure sensing device may be coupled to a third lumen and connector 16 to a pressure monitoring device 20. When the coronary sinus is blocked by balloon 12, blood flows from the sinus through port 14 and the central lumen of catheter 10 to a blood filtration device 16 which separates the contrast solution and water from the blood. An equal volume of water or other appropriate crystalloid is then added to the blood which can be re-infused to the patient in the femoral vein.

Figure 3:
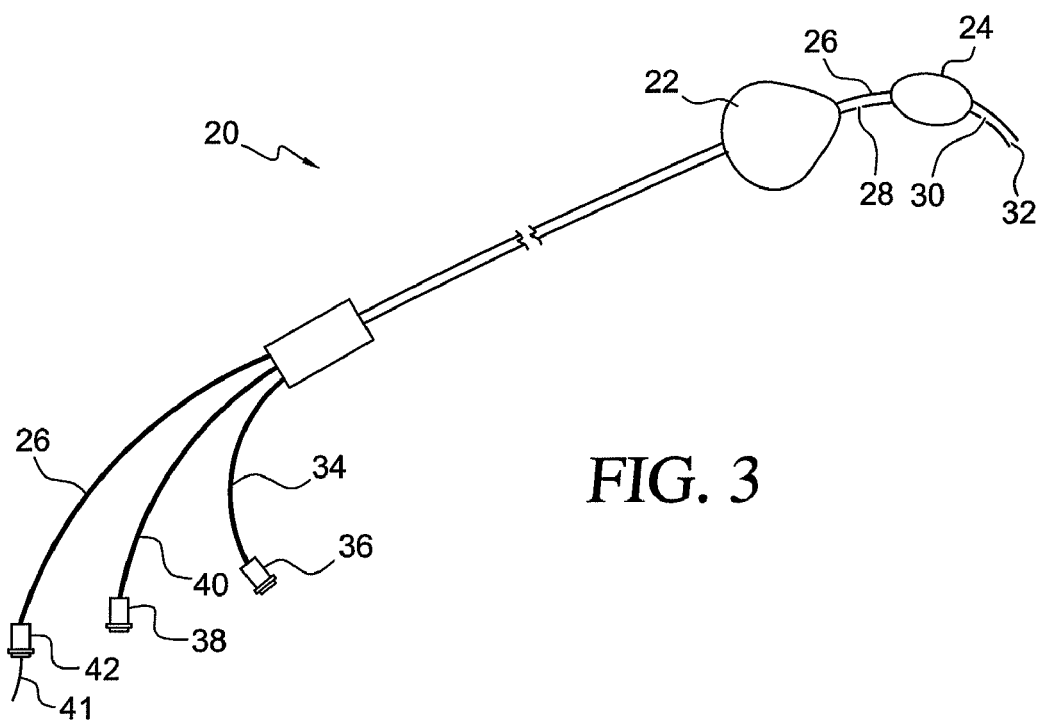
FIG. 3 is a schematic illustration of a multi-lumen double balloon catheter in accordance with the present invention.
Figure 4:
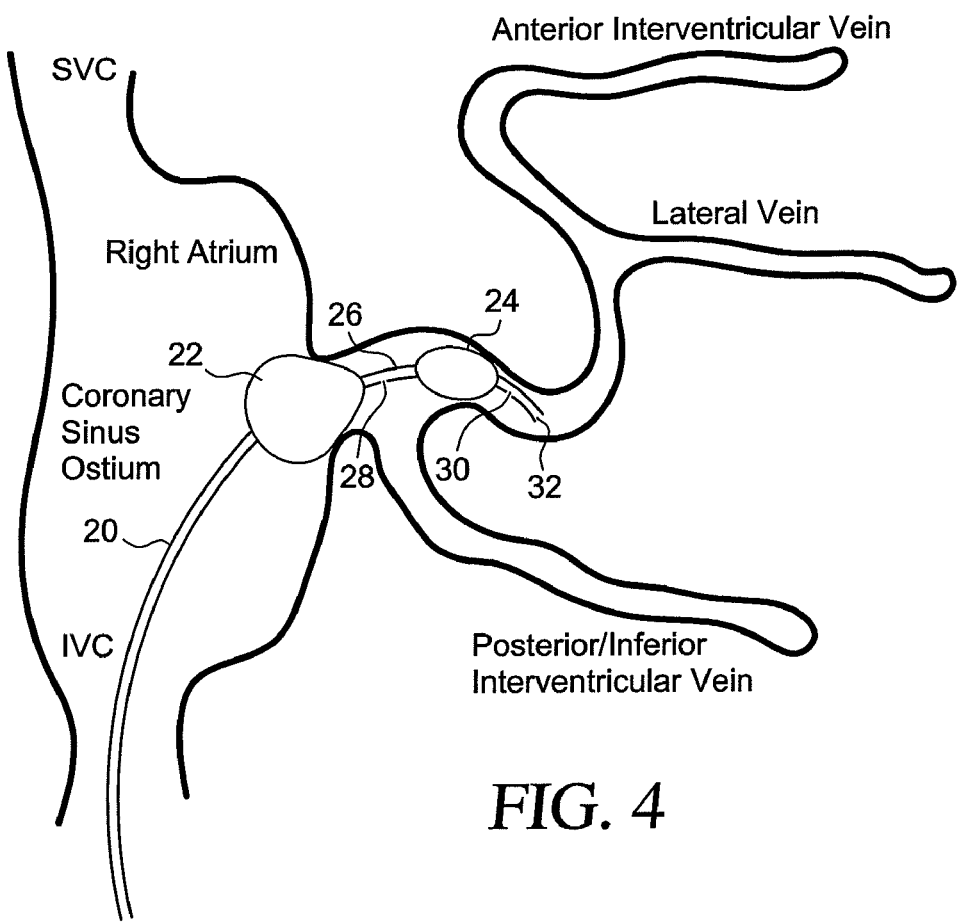
FIG. 4 is a schematic diagram of a dye drain double balloon catheter in a coronary venus system in accordance with the present invention.

A catheter 20 in accordance with the present invention is illustrated in FIGS. 3 and 4. As shown, the catheter 20 is a multi-lumen dual balloon catheter having two balloons 22 and 24 connected together by a lumen 26 that passes through the balloons 22 and 24 and defines a central lumen port 28 between the balloons 22 and 24. A second lumen port 30 is also provided in the lumen 26 between the second balloon 24 and the distal end 32 of the lumen 26 adjacent to the balloon 24.

The balloon 22 is the larger of the two balloons and is made of a compliant material with a tapered shape and a diameter of about 20-30 mm at its widest part. The shape and size are designed to conform to a patient's coronary sinus ostium. By contrast, the smaller balloon 24 has a diameter of about 8-10 mm and is also made of a compliant material. The smaller balloon 24 is designed and constructed to fit within the sinus and to hold the larger balloon 22 in place and to isolate or block the lateral vein and the anterior inter-ventricular vein as shown in FIG. 4.

As shown in FIG. 3, the catheter 20 also includes an inflation port 36 at the end of a first lumen 34 and is connected to the balloon 22 for inflation and deflation of the balloon 22. The catheter 20 also includes a second inflation port 38 for a second lumen 40 that is connected to the second balloon 24 for inflation and/or deflation of the balloon 24. In addition to the above, the catheter 20 includes a central lumen port 42 at one end of lumen 23 that is provided with a 0.035 inch guide wire. The port 42 is used for suction to drain the blood/contrast solution through the ports 28 and 30 and lumen 26 to avoid the risk of contrast associated nephropathy.

FIG. 4 also illustrates the venus drainage into the right atrium and the dye drain system in accordance with the present invention. As shown, the dye drain system acts as a closed circuit to remove the contrast contaminated blood to prevent its arrival at the kidneys. Thus, it avoids contrast induced nephropathy in high risk patients.

Figure 5:
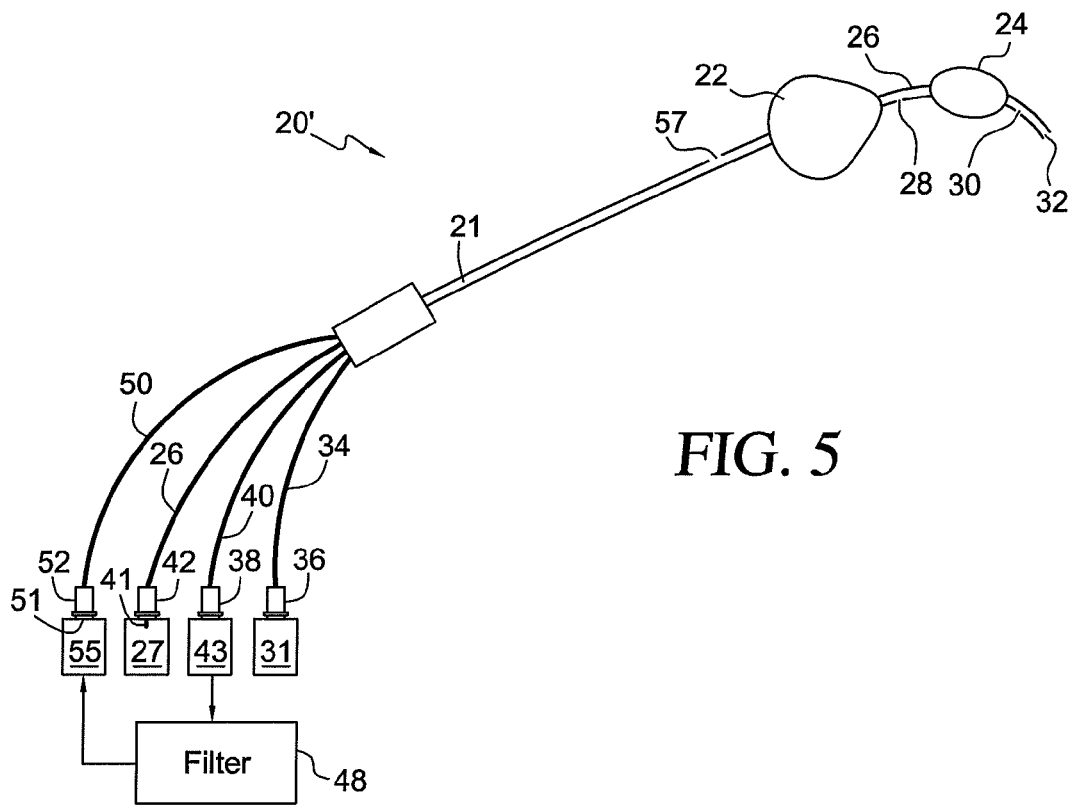
FIG. 5 is a schematic illustration of a multi-lumen double balloon catheter in accordance with a second embodiment of the invention.

A further embodiment of the invention is illustrated in FIG. 5 and is in general similar to the embodiment shown in FIGS. 3 and 4. However, in this embodiment of the invention, the blood containing contrast solution from lumen 42 passes through a pressure monitoring device 43 and into a hemo-filtration unit 48 for removal of the contrast solution from the blood. In this embodiment of the invention, a fourth lumen 50 and port 52 are provided for returning blood to the right atrium of a patient's heart. A suitable pump 44 may be used to return the filtered blood to the patient. Inflation, deflation devices such as push/pull syringes 27 and 31 are used to inflate or deflate the balloons.

Regarding balloon inflation sequences: it occurs in two ways a—for transient occlusion catheters, both balloons are inflated simultaneously after contrast injection in the coronary arteries and deflated once the contrast is drained from the accumulation chamber in the coronary sinus. this is very brief occlusion and probably for 10-30 heart beats. b—in case of continuous occlusion catheters as in modifications 1 and 3 the balloons remain occlusive throughout the procedure and drainage is directed to a hemofiltration unit for dye separation and returning the purified blood to right atrium. in this case drainage by pump of hemofiltration unit from the accumulation chamber while the balloon are occlusive ensures blood circulation through the heart vasculature.

Figure 6:
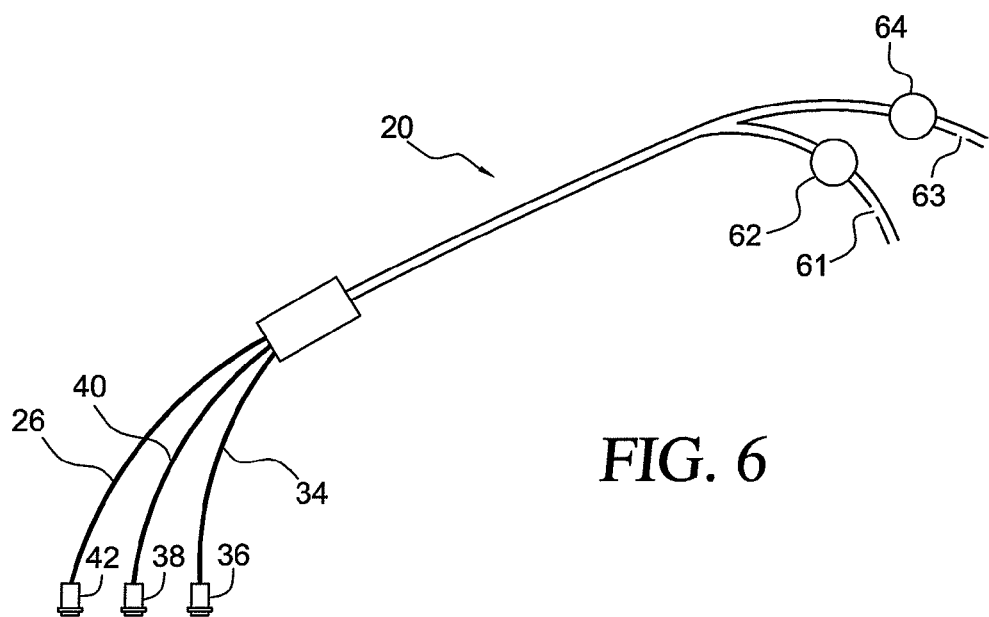
FIG. 6 is a schematic illustration of a third embodiment of the invention.

FIG. 6 illustrates another embodiment of the invention wherein a catheter 20 includes three lumens 23, 34 and 40 which serve the same function as the catheter 20 in FIG. 3. This embodiment of the invention addresses the proximity of the interior coronary vein to the coronary sinus ostium by selectively occluding both the sinus in the groove and the inferior vein and directing the drainage in a similar manner as in the earlier embodiment. However, in this embodiment, the two balloons 62 and 64 are positioned in the inferior coronary vein and the sinus ostium respectively and the blood and contrast solution are drained there from to a pair of ports 61 and 63.

Figure 7:
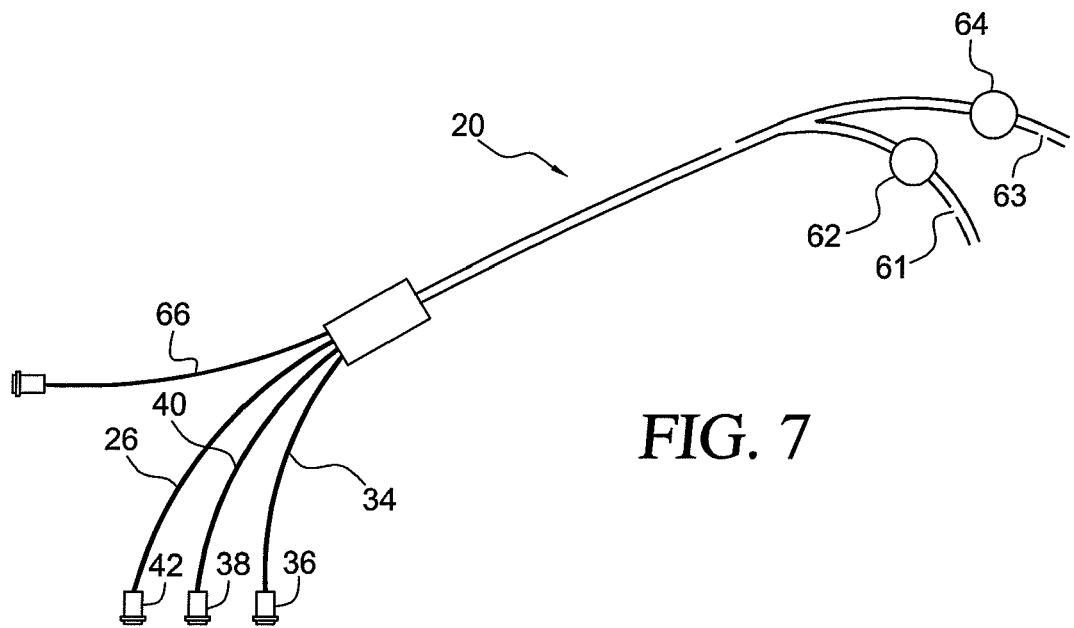
FIG. 7 is a schematic illustration of a fourth embodiment of the invention.

A still further embodiment of the invention is illustrated in FIG. 7 where a catheter 20 is generally similar to the catheter 20 shown in FIGS. 5 and 6. In this modification of the earlier catheter of FIG. 5, a fourth lumen 50 and port or opening 52 are used to return filtered blood from the hemo-filtration unit 48 as shown in FIG. 5 to the right atrium of a patient's heart. Also, the balloons 62 and 64 are used as in FIG. 6.

Figure 8:
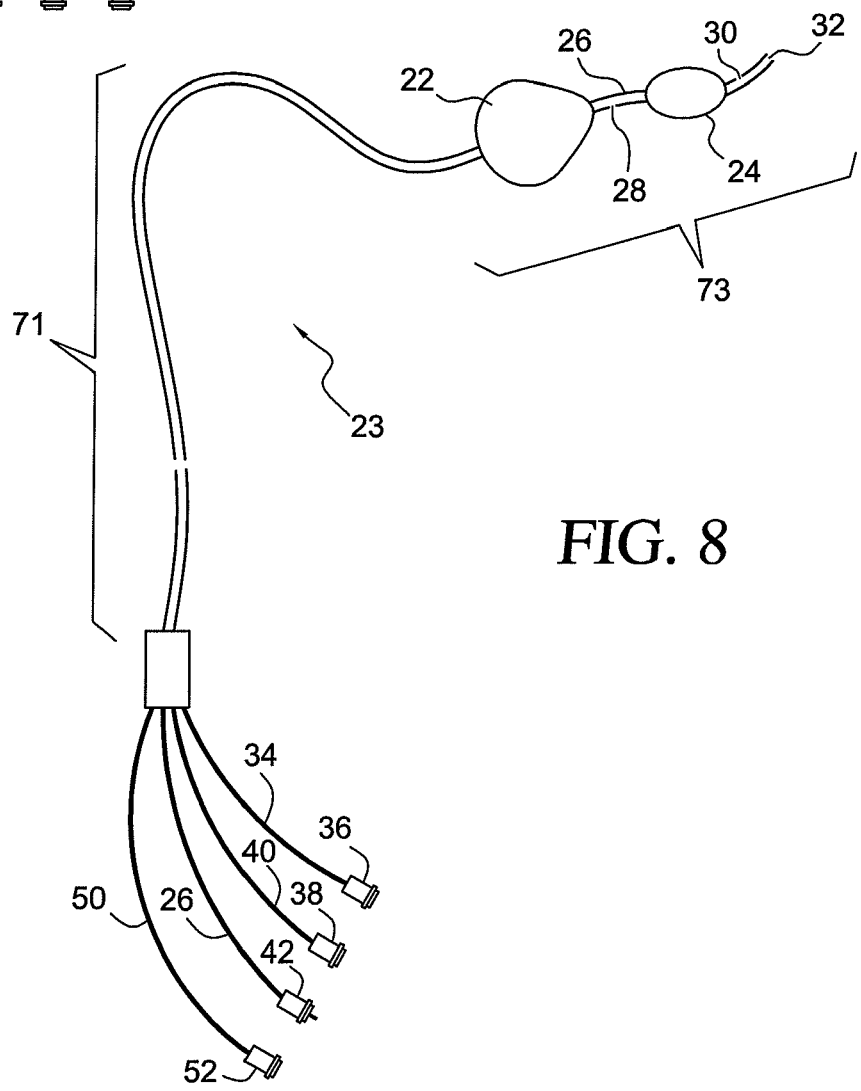
FIG. 8 is a schematic illustration of a fifth embodiment of the invention.

An additional embodiment of the invention is shown if FIG. 8 and contemplates the use of a modified catheter 23 which includes most of the same elements as shown in the embodiment of FIG. 5. For example, the catheter 23 includes a tapered balloon 22 and smaller spherical balloon 24 and ports 28 and 30 for draining blood and contrast solution from the coronary sinus. However, in this embodiment, the catheter 23 includes an outer sheath or support staff 71 and a soft and more flexible body portion 73. The support staff 71 extends over most of the catheter that is prior to the balloon 22, while the flexible portion 73 extends from the front of the balloon 22 to the distal end 32.

Figure 9:
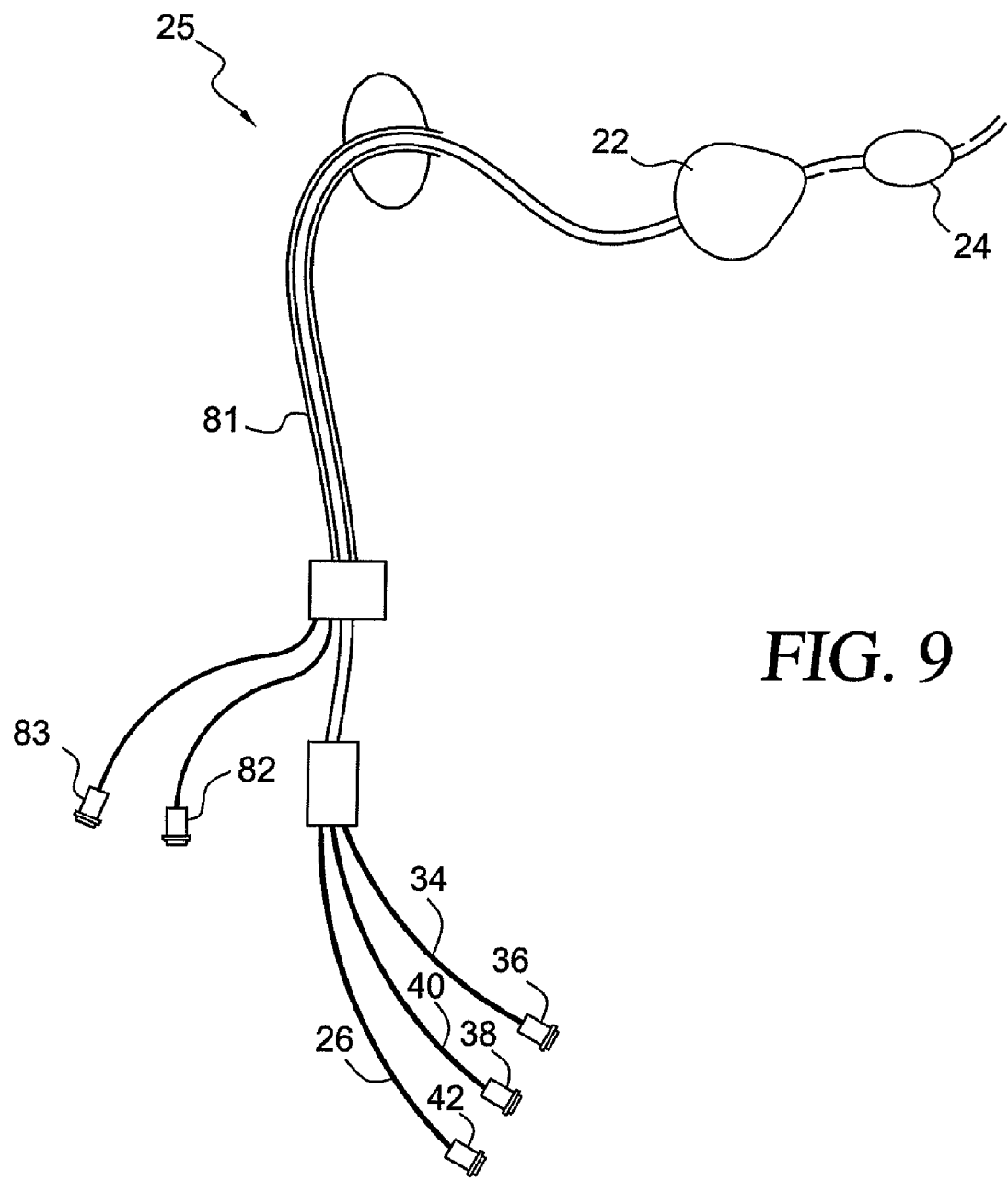
FIG. 9 is a schematic illustration of a sixth embodiment of the invention.

A still further embodiment of the invention is illustrated in FIG. 9 and is a further modification of the catheter shown in FIG. 8. As shown in FIG. 9 the catheter 25 includes a sheath distal tip occlusion balloon 80 that alleviates any blood leakage from the sides of the sheath. A sheath shaft support 81, a balloon inflation port 82 and a suction port 83 at the end of a lumen running from the tip of the sheath to the coronary sinus are provided.

Figure 10:
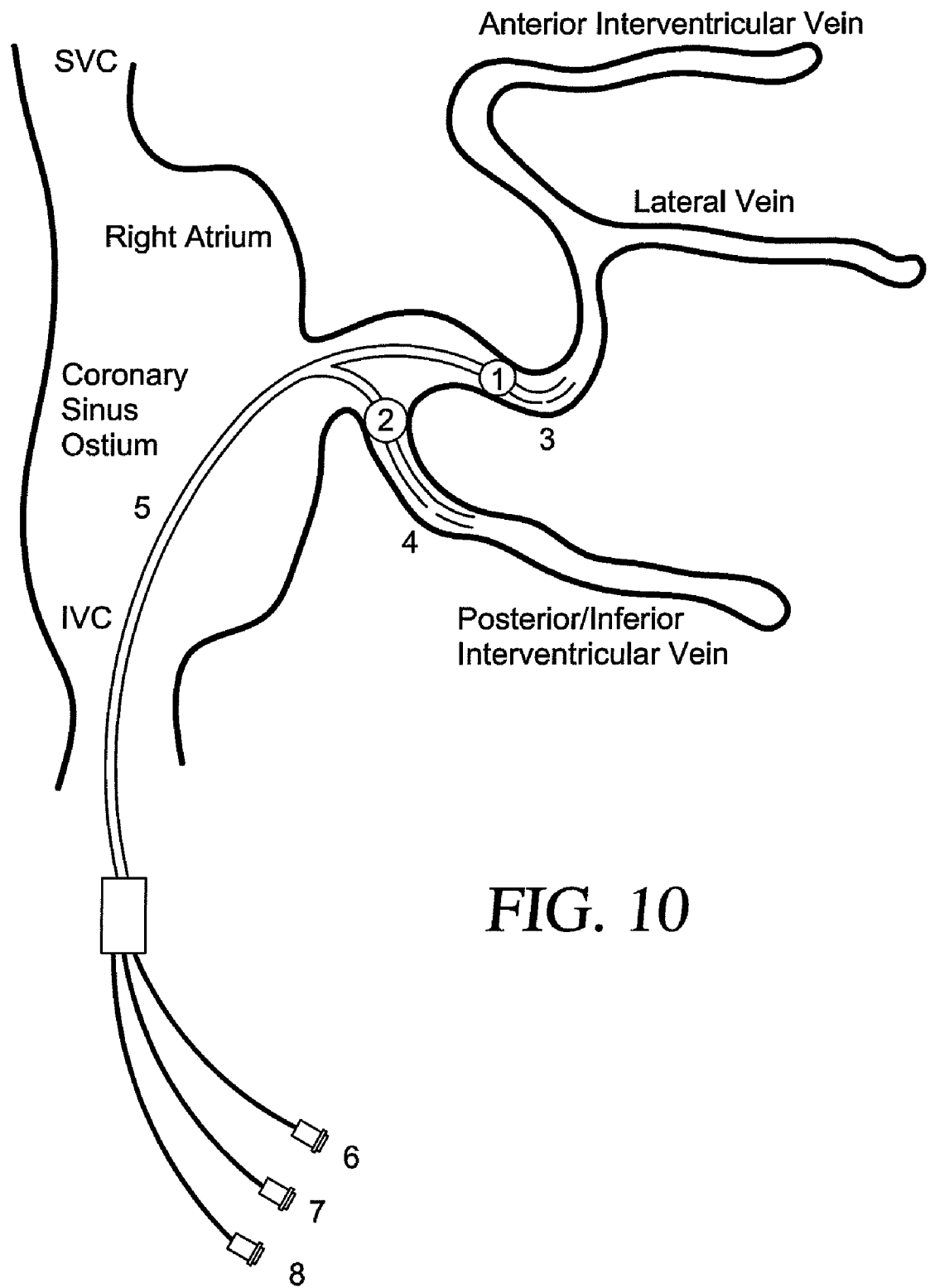
FIG. 10 is a schematic diagram of a double balloon catheter in a coronary venus system in accordance with the 3rd and 4th embodiments of the invention.

FIG. 10 shows the catheter 20 in accordance with the $3^{rd}$ embodiment of the invention as positioned within a patient. As shown, a parallel balloon system provides continuous occlusion of the venus drainage. In this design, the drained blood is directed to a hemofiltration system that allows filtered blood to be returned to the circulation via the right atrial port. To be more specific, the balloon 62 is positioned between the patient's posterior/inferior interventricular vein and the lateral vein while the balloon 64 is positioned in the posterior/inferior interventricular vein or at an entrance thereof. The balloons 62 and 64 are inflated to prevent blood containing contrast solution from flowing into the right atrium of the heart and for draining the blood and contrast solution as described above.

While the invention has been described in connection with its preferred embodiments, it should be recognized that changes and modifications may be made therein without departing from the scope of the appended claims.

What is claimed is:

1. A method for preventing contrast associated nephropathy comprising the steps of:
   providing a dual balloon multi-lumen catheter having a first lumen, a larger tapered balloon and a smaller spherical balloon connected to the larger tapered balloon by the first lumen and a suction orifice defined in the first lumen between the two balloons;
   providing a first inflation port for the larger tapered balloon and a second inflation port for the smaller spherical balloon and a third lumen connected to the port for draining blood from between the balloons;
   inflating the balloons after introducing a contrast solution into a patient's blood stream and removing blood containing contrast solution from between the two balloons; and
   including the steps of anchoring the catheter in place in a patient's coronary sinus with the smaller spherical balloon, inflating the larger tapered balloon when the contrast solution is introduced into the patient and deflating the larger taper balloon when the blood between the balloons has been removed.

2. A method for preventing contrast associated nephropathy according to claim 1 which includes the steps of extending the lumen connecting the balloons beyond the smaller spherical balloon and providing a second orifice in the extension of said lumen adjacent the spherical balloon for removing blood containing contrast solution from the anterior inter-ventricular vein and the lateral vein through the second orifice.

3. A method for preventing contrast associated nephropathy according to claim 2 which includes the step of hemo filtering the blood removed from the anterior inter-ventricular vein and lateral vein and returning the hemo filtered blood to the patient's bloodstream.

4. A method for providing contrast associated nephropathy according to claim 1 which includes the steps of providing a support shaft to provide a stiffer distal portion and a softer leading portion.

5. A dual balloon catheter for preventing contrast associated nephropathy according to claim 1 which includes a guide wire.

* * * * *